United States Patent [19]

Regnir et al.

[11] Patent Number: 5,066,651
[45] Date of Patent: Nov. 19, 1991

[54] PYRROLIDONE COMPOUNDS FOR TREATING CEREBRAL DISORDERS

[75] Inventors: Gilbert Regnir, Chatenay Malabry; Alain Dhainaut; Jean Lepagnol, both of Chatout, all of France; Jean Lepagnol, both of Chatou, France

[73] Assignee: Adir et Compagnie, Courbevoie, France

[21] Appl. No.: 525,137

[22] Filed: May 17, 1990

[30] Foreign Application Priority Data

May 31, 1989 [FR] France ................... 89 07153

[51] Int. Cl.$^5$ ............... A61K 31/495; A61K 31/535; A61K 31/54; A61K 31/425
[52] U.S. Cl. ................... 514/235.5; 514/237; 514/252; 514/254; 514/326; 514/422; 514/425; 544/58.6; 544/82; 544/141; 544/295; 544/333; 544/357; 544/360; 544/361; 544/362; 544/363; 544/364; 544/369; 544/372; 544/405; 546/193; 546/194; 548/206; 548/208; 548/542
[58] Field of Search ............ 544/141, 372, 357, 58.6, 544/82, 295, 333, 360–364, 369; 548/542, 206; 514/235.5, 252, 425, 237.2, 422, 326, 254; 546/208, 193, 194

[56] References Cited
PUBLICATIONS

Toja et al., Chem Abst. 108-5855r (1988).
G. A. Wiley et al. JACS, vol. 86, 964 (1964).

*Primary Examiner*—Cecilia Shen
*Attorney, Agent, or Firm*—Gordon W. Hueschen

[57] ABSTRACT

New pyrrolidone compounds of the formula:

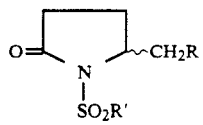

in which:
R is OR", SR" or N ($R_3R_4$)
R' is optionally substituted alkyl or aryl, and
the carbon in the 5-position of the pyrrolidone ring, which is substituted by $CH_2R$ has the R or S configuration.

These new compounds and their physiologically tolerable salts may be used therapeutically especially in the treatment of asthenias, ischaemic syndromes and nervous disorders associated with normal or pathological ageing.

12 Claims, No Drawings

PYRROLIDONE COMPOUNDS FOR TREATING CEREBRAL DISORDERS

The present invention provides pyrrolidone compounds of the general formula I:

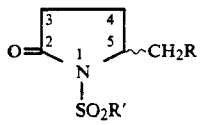

(I)

in which:
R is selected from the group consisting of:
a) OR" and SR" groups in which R" is selected from the group consisting of:
  a hydrogen atom,
  a COR''' radical in which R''' is selected from the group consisting of:
    straight-chain and branched alkyl radicals having from 1 to 4 carbon atoms,
  a —N ($R_1R_2$) radical in which $R_1$ and $R_2$, which are the same or different, are each selected from the group consisting of straight-chain and branched alkyl radicals having from 1 to 5 carbon atoms, and $R_1$ and $R_2$ together represent a polymethylene chain having from 4 to 6 carbon atoms, and such a chain containing an oxygen atom, so as to form together with the nitrogen atom to which they are bonded a heterocyclic radical selected from pyrrolidinyl, piperidino and morpholino radicals;
  straight-chain and branched alkyl groups having from 1 to 6 carbon atoms, and these groups containing one and more oxygen atoms, a hydroxy radical and a—N ($R_1R_2$) radical in which $R_1$ and $R_2$ have the meanings defined above;
b) a—N ($R_3R_4$) radical in which:
  $R_3$ and $R_4$ which are the same or different, are each selected from the group consisting of:
    a hydrogen atom,
    straight-chain and branched alkyl radicals having up to 6 carbon atoms and these radicals containing one and more oxygen atoms, a hydroxy radical, —O COR''' and —N ($R_1R_2$) radicals in which R''', $R_1$ and $R_2$ have the meanings defined above, and
  $R_3$ and $R_4$ together with the nitrogen atom to which they are bonded, form a heterocyclic radical of the formula:

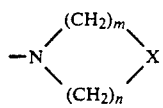

in which:
m is selected from zero, one and two;
n is an integer of from 1 to 3, and
x is selected from the group consisting of:
  a methylene radical (—$CH_2$—);
  oxygen and sulfur atoms, and the radical $SO_2$;
  a N-$R_5$ radical in which $R_5$ is selected from the group consisting of:
    alkyl radicals having from 1 to 4 carbon atoms,
    an hydroxy alkyl radical having from 1 to 4 carbon atoms,
    an (unsubstituted aryl)-alkyl radical in which the alkyl moiety has from 1 to 4 carbon atoms, and such aralkyl radicals in which the aryl moiety is mono and polysubstituted by ($C_1$-$C_4$) alkoxy and methylenedioxy radicals,
    unsubstituted aryl radicals and such aryl radicals mono and polysubstituted by halogen atoms, and ($C_1$-$C_4$) alkoxy radicals, and
    heterocyclic radicals, having one and two heteroatoms, selected from thiazolyl, pyrimidinyl, pyrazinyl, pyridyl and quinolyl radicals and such radicals mono and poly-substituted by halogen atoms, trifluoromethyl and ($C_1$-$C_4$) alkoxy radicals; and
  a >CH—YZ radical in which:
    Y is selected from oxygen and sulfur atoms, and
    Z is selected from heterocyclic radicals having one and two heteroatoms as defined above;
R' is selected from the group consisting of:
  a) straight-chain and branched alkyl radicals having from 1 to 4 carbon atoms, such radicals containing a double bond, and such radicals mono and polysubtituted by hydroxy, trifluoromethyl, amino, —N ($R_1R_2$) as defined above, phenyl halophenyl, ($C_1$-$C_5$-alkyl) phenyl, ($C_1$-$C_5$alkoxy) phenyl, nitrophenyl and aminophenyl radicals; and
  b) aryl, halo-aryl, ($C_1$-$C_5$-alkyl)-aryl, ($C_1$-$C_5$-alkoxy)-aryl, nitroaryl and amino-aryl radicals; and
    the carbon located in the 5-position of the pyrrolidine ring, which is substituted by $CH_2R$, has the R or S configuration depending on whether the synthesis starting material is natural pyroglutamic acid having the R or S configuration.

The prior art is illustrated especially by the European Patent Application published under No. 0 229 566 which relates to 1-benzenesulphonyl-2-oxopyrrolidines which are always substituted in the 5-position by an ether function and which can be used as medicaments in the treatment of intellectual or nervous asthenias, lapses of memory, senescence and mental strain.

The compounds of the present invention differ from the compounds of European Application No. 0 229 566 in that they never have an ether function bonded directly to the pyrrolidine nucleus. However, they have an especially valuable pharmacological and therapeutic activity, as is demonstrated by the pharmacological study described in Example 63.

The present invention relates also to a process for the preparation of the compounds of the general formula I, which process is characterised in that a pyrrolidone compound of the general formula II:

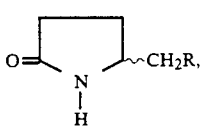

(II)

in which R has the meaning defined above, is reacted with a sulphonyl chloride of the general formula III:

 (III)

in which R' has the meaning defined above.

It is especially advantageous to react the compound II, which is first converted into a sodium or lithium derivative by means of sodium hydride or butyllithium hydride, respectively, with the sulphonyl chloride III at ambient temperature in a polar aprotic solvent, such as, for example tetrahydrofuran, dioxane, dimethyl sulphoxide, dimethylformamide or a mixture thereof.

The present invention relates also to a variant of the above process more especially for the preparation of the compounds of formula I in which R represents

that is to say a process for the preparation of the compounds I having the general formula I':

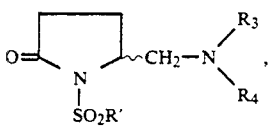 (I')

in which R', R$_3$ and R$_4$ have the meanings as defined above, which process is characterised in that a pyrrolidone compounds of the general formula IV:

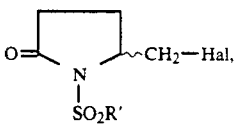 (IV)

in which R' has the meaning defined above and Hal' represents a chlorine or bromine atom, is reacted with a secondary amine of the general formula V:

 (V)

in which R$_3$ and R$_4$ have the meanings defined above.

It is especially suitable to carry out the reaction by heating the compounds (IV) and (V) in a polar solvent, such as, for example, a high-boiling alcohol, dimethylformamide or dimethylacetamide, at a temperature of from 110° to 150° C. in the presence of an acceptor for the hydracid formed during the reaction. The acceptor may be a tertiary base, such as, for example, triethylamine or ethyldipropylamine, or an excess of the secondary amine (V), which may also serve as the solvent for the reaction.

The starting materials of formula II in which R represents OR" or SR" can be prepared in simple manner by debenzylating, by means of sodium in liquid ammonia (in accordance with a conventional method), the compound of the general formula VI:

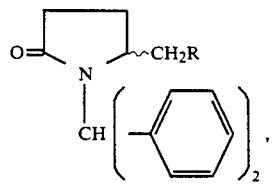 (VI)

in which R has the meaning defined above, which is itself prepared by reacting a compound of the formula R"Hal, in which R" has the meaning defined above and Hal represents a bromine or iodine atom or a tosyloxy radical, with an R or S pyroglutaminol compound [which is itself prepared according to S. SAIJO, M. WADA, J. HIMIZU and A. ISHIDA—Chem. Pharm. Bull. 28 (5) 1449–1458 (1980)] of the formula VII:

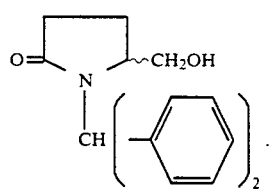 (VII)

The compound VII is prepared by controlled hydrolysis, with HCl or (COOH)$_2$ in a dilute alcoholic medium, or the compound of the formula VIII:

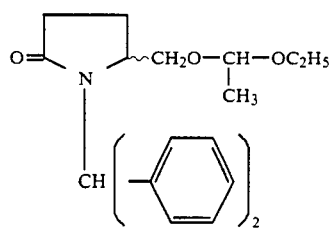 (VIII)

which is itself prepared by the condensation of benzhydryl bromide with the compound of the formula IX:

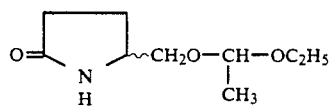 (IX)

which is itself prepared [according to S. SAIJO et al., Bull. Pharm. Soc. 28 (5) 1449–1458 (1980)] by the action of ethyl vinyl ether, in CHCl$_3$ at ambient temperature in the presence of CCl$_3$COOH, on R or S pyroglutaminol.

The starting materials of formula II in which R represents

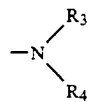

can be prepared by heating a halogenated compound of the formula X:

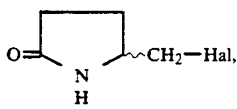 (X)

in which Hal represents a chlorine or bromine atom [which is itself prepared according to G. WILEY et al., J. Am. Chem. Soc. 86, 964 (1964), using $P(C_6H_5)_3$—$CCl_4$ or $P(C_6H_5)_3Br_2$ in dimethylformamide] with an amine of the formula:

in which $R_3$ and $R_4$ have the meanings defined above.

The starting materials of formula IV can readily be prepared by halogenation, according to the above-mentioned method, of compounds of the formula XI:

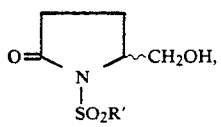 (XI)

in which R' has the meaning defined above, which are themselves prepared by controlled hydrolysis of the compounds of the formula XII:

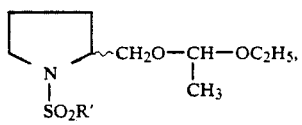 (XII)

in which R' has the meaning defined above, which compounds XII are themselves prepared from a sulphonyl halide III and the compound IX.

All these compounds can be purified by conventional chemical methods, such as distillation, crystallisation in the salt form when the molecule (I) contains a basic group of the

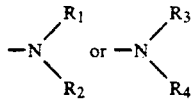

type that is capable of forming crystallised salts, or alternatively by flash chromatography on a silica support (35–70 μ) with elution systems such as $CH_2Cl_2$-methanol, $CH_3COOC_2H_5$-methanol, $CH_3COOC_2H_5$, etc. under nitrogen pressures of from 0.5 to 1 bar.

The compounds of the invention of which the formula I contains a basic group of the

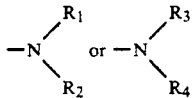

type may be converted into addition salts with acids, which salts therefore form part of the present invention. Examples of acids that can be used for the formation of those salts are, in the mineral series: hydrochloric, hydrobromic, sulphuric and phosphoric acids, and in the organic series: acetic, propionic, maleic, fumaric, tartaric, citric, benzoic and methanesulphonic acids.

The compounds of the general formula I and their physiologically tolerable salts have valuable pharmacological and therapeutic properties.

In particular, they combat cerebral disorders associated with a lack of energy as a result of an insufficient oxygen intake, or associated with a metabolic neuronal deficiency. Accordingly, they may be used in the treatment of asthenias, acute, transitory or progressive ischaemic syndromes, and nervous disorders associated with normal or pathological ageing, such as Alzheimer's disease. The unit dosage may be from 1 to 1000 mg for treatment in 1 to 3 doses per day.

The present invention relates also to pharmaceutical compositions containing as active ingredient a compound of the general formula I or one of its physiologically tolerable salts, in admixture or in association with a suitable pharmaceutical excipient, such as, for example, distilled water, glucose, lactose, starch, talcum, ethylcellulose, magnesium stearate or cocoa butter. The pharmaceutical compositions thus obtained are generally in dosage form and may contain from 1 to 1000 mg of active ingredient. They may be in the form of tablets, dragées, gelatin-coated pills, drinkable solutions, injectable solutions or suppositories and, depending on each individual case, may be administered in a dose of from 1 to 1000 mg from 1 to 3 times per day.

The following Examples illustrate the invention. Melting points are determined in a capillary tube.

EXAMPLE 1

S-1-Benzenesulphonyl-2-Oxo-5-Morpholinomethylpyrrolidine

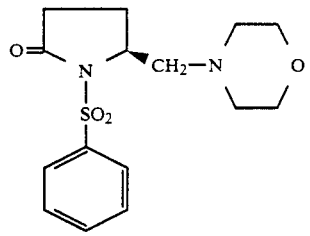

A) 1st Method 7 ml of BuLi (1.6M) dissolved in hexane are added at 10° C., under nitrogen, to a solution of 1.85 g of S-5-morpholinomethyl-2-pyrrolidone (which melts at 74°–77° C.) in 20 ml of anhydrous tetrahydrofuran. The mixture is stirred at ambient temperature for 30 minutes and then 1.8 g of benzenesulphonyl chloride are added, the temperature being maintained at 15° C. The mixture is stirred for a further 15 hours at laboratory temperature, and then the solvent is evaporated off under reduced pressure. The residue is taken up in 20 ml of water and 20 ml of $CH_2Cl_2$. The mixture is decanted and dried over $MgSO_4$, and the evaporation residue is purified by flash chromatography over $SiO_2$ with 100% $CH_3COOC_2H_5$ as eluant.

In this manner, 1.6 g of S-1-benzenesulphonyl-2-oxo-5-morpholinomethylpyrrolidine crystals are isolated. The S-5-morpholinomethyl-2-pyrrolidone used as starting material [$\alpha_D^{20.5} = +48.3°$ (c=1 $C_2H_5OH$)] was prepared in a yield of 78% by heating S-5-chloromethyl-2-pyrrolidone (m.p.: 54°-56° C.) under reflux in morpholine, the chloromethyl compound itself being prepared from S-pyroglutaminol by the $(C_6H_5)_3P-CCl_4$ method in a yield of 86%.

R-1-benzenesulphonyl-2-oxo-5-morpholinomethyl-pyrrolidine is obtained in the same manner using R-5-morpholinomethyl-2-pyrrolidone (in place of S-5-morpholinomethyl-2-pyrrolidone).

B) 2nd Method

A solution of 2.7 g of S-1-benzenesulphonyl-5-chloromethyl-2-pyrrolidone in morpholine is heated under reflux for 3 hours. The excess morpholine is then expelled under reduced pressure and the residue is taken up in $H_2O$. The crystals are suction filtered and dried in vacuo. There are obtained 3.1 g of S-1-benzenesulphonyl-2-oxo-5-morpholinomethylpyrrolidine crystals, which melt at 113°-114° C. The chloromethyl derivative (oil) used as starting material was prepared by the $P(C_6H_5)_3$-$CCl_4$-dimethylformamide method in a yield of 85%, starting from S-1-benezenesulphonylpyroglutaminol, m.p.: 104°-105° C., $\alpha_D < : -51.2°$ (c=1 $CH_3OH$).

EXAMPLE 2

S-1-Benzenesulphonyl-2-Oxo-5-Hydroxymethylpyrrolidine

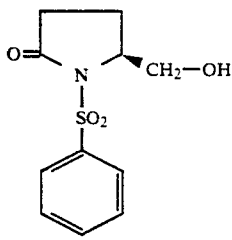

232 ml of a 1.6M solution of BuLi in hexane are added at 10° C. to a solution of 63.1 g of S-1-ethoxy-5-ethoxymethyl-2-pyrrolidone in 150 ml of anhydrous tetrahydrofuran. The mixture is stirred for 30 minutes and then 100 ml of DMSO are added. 59.5 g of benzenesulphonyl chloride are added to that solution at 10°-15° C. over a period of 30 minutes, and then the mixture is left at ambient temperature overnight. The solution is then diluted with 1 liter of water and extracted several times with $CH_2Cl_2$. The extract is washed with water and dried over $MgSO_4$; then the solvent is evaporated off under reduced pressure and 5 g of oil are isolated and dissolved in 300 ml of methanol. 100 ml of 0.1N HCl are added and the solution is stirred at ambient temperature for 15 hours. The solvent is evaporated off and the residue is purified by flash chromatography over 1.2 kg of silica with $CH_3COOC_2H_5$-$CH_2Cl_2$ (3-7) as eluant. There are isolated 20 g of S-1-benzenesulphonyl-2-oxo-5-hydroxymethylpyrrolidine crystals, which melt at 104°-105° C., $\alpha_D^{21}: -51.2°$(c=1 $CH_3OH$).

The S-1-ethoxy-5-ethoxymethyl-2-pyrrolidone used as starting material [$\alpha_D^{20.5}: = +21.8°$ (c=1 $C_2H_5OH$)] was prepared in yields of from 83 to 97% by the action of ethyl vinyl ether on S-pyroglutaminol in $CHCl_3$ in the presence of trichloroacetic acid.

EXAMPLE 3

S-1-Benzenesulphonyl-2-Oxo-5-Methoxymethylpyrrolidine

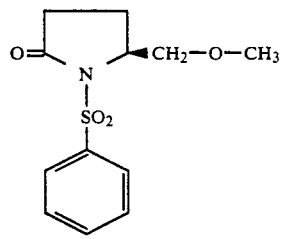

Following the procedure described in Example 1, first method, 4.6 g of S-1-benzenesulphonyl-2-oxo-5-methoxymethylpyrrolidine crystals which melt at 88° C. are obtained from 5.7 g of S-5-methoxymethyl-2-pyrrolidone (oil); $\alpha_D^{22} = -74.6°$ (c=1 $CH_3OH$).

The methoxymethyl derivative used as starting material [$\alpha_D^{29}: +40°$ (c=1 $C_2H_5OH$)] was prepared by the debenzhydrylation, by means of sodium in liquid $NH_3$, of S-1-benzhydryl-5-methoxymethyl-2-pyrrolidinone, which was itself prepared by the action of methyl tosylate on S-1-benzhydryl-5-hydroxymethyl-2-pyrrolidinone [m.p.: 105°-180° C.; $\alpha_D^{20.5} = -86°$ (c=1 $C_2H_5OH$)], which was itself prepared by the controlled hydrolysis, with $(COOH)_2$ in methanol, of S-1-benzhydryl-5-(1-ethoxy-ethoxymethyl)-2-pyrrolidinone (oil), which was itself prepared, as indicated in Example 1, first method, from bromodiphenylmethane and 5-(1-ethoxy-ethoxymethyl)-2-pyrrolidone.

EXAMPLE 4

S-1-Benzenesulphonyl-2-Oxo-5[(4-Methyl-1-Piperazinyl)Methyl]-Pyrrolidine

The physical constants of the dihydrochloride being: m.p.: 230° C.; $\alpha_D^{21} = -42.4°$ (c=1% $CH_3OH$), prepared as described in Example 1, first method, from S-5-[(4-methyl-1-piperazinyl)methyl]-2-pyrrolidone (oil).

EXAMPLE 5

S-1-Benzenesulphonyl-2-Oxo-5-{[4-(2,3,4-Trimethoxybenzyl)-1-Piperazinyl]Methyl}-Pyrrolidine The constants of the dihydrochloride being: m.p.: 235°-238° C.; $\alpha_D^{20} = -21.7°$ (c=1%, $H_2O$), prepared as described in Example 1, first method, from S-5-{[4-(2,3,4-trimethoxybenzyl)-1-piperazinyl]methyl}-2-pyrrolidone (oil).

EXAMPLE 6

S-1-Benzenesulphonyl-2-Oxo-5-[(4-Metatrifluoromethylphenyl-1-Piperazinyl)Methyl]-Pyrrolidine The physical constants of the fumarate being: m.p.: 151° C.; $\alpha_D^{20} = -36.9°$ (c=1%, $C_2H_5OH$), prepared as described in Example 1, first method, from S-5-[(4-metatrifluoromethylphenyl-1-piperazinyl)methyl]-2-pyrrolidone.

EXAMPLES 7-36

The compounds shown in the table below were prepared by the process described in Example 1, first method:

Pyrrolidone compounds of the formula:
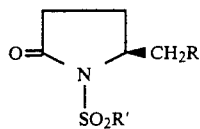
| EXAMPLE | R | R' |
|---|---|---|
| 7 | —OC$_2$H$_5$ | phenyl |
| 8 | —O—CH(CH$_3$)$_2$ | " |
| 9 | —O—(CH$_2$)$_4$—CH$_3$ | " |
| 10 | —O—CH$_2$CH$_2$OH | " |
| 11 | —O—CH$_2$CH$_2$OCH$_3$ | " |
| 12 | —O—CH$_2$—CH$_2$—N(CH$_3$)$_2$ | " |
| 13 | —OCH$_2$CH$_2$—N(morpholino) | " |
| 14 | —N(piperazinyl)-pyrimidin-2-yl | " |
| 15 | —N(piperazinyl)—N—CH$_2$-(1,3-dioxolo[4,5-b]pyridinyl) | " |
| 16 | —N(piperazinyl)-quinolin-2-yl | " |
| 17 | —N(piperazinyl)-(3-chloropyrazin-2-yl) | " |
| 18 | —N(pyrrolidinyl) | " |
| 19 | —N(piperidin-4-yl)-S-(pyridin-2-yl) | " |

-continued
Pyrrolidone compounds of the formula:
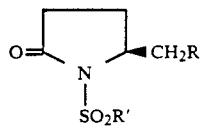
| EXAMPLE | R | R' |
|---|---|---|
| 20 | —NHCH₂CH₂N(CH₃)₂ | " |
| 21 | —N(CH₃)₂ | " |
| 22 | —SH | " |
| 23 | —S—CO—CH₃ | " |
| 24 | —O—COCH₃ | " |
| 25 | —OCON(C₂H₅)₂ | " |
| 26 | —N(morpholine) | 4-Br-C₆H₄— |
| 27 | " | 4-F-C₆H₄— |
| 28 | " | 2,4-Cl₂-C₆H₃— |
| 29 | " | 4-CH₃-C₆H₄— |
| 30 | " | 2,3-(CH₃)₂-C₆H₃— |
| 31 | " | 4-OCH₃-C₆H₄— |
| 32 | " | 4-NO₂-C₆H₄— |

-continued
Pyrrolidone compounds of the formula:
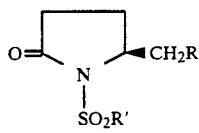
| EXAMPLE | R | R' |
|---|---|---|
| 33 | " | —⟨C6H4⟩—NH2 |
| 34 | " | —CH3 |
| 35 | " | —CH2—CH3 |
| 36 | " | —CH(CH3)2 |
| 37 | " | —(CH2)3—CH3 |
| 38 | " | —(CH2)6—CH3 |
| 39 | " | —(CH2)9—CH3 |
| 40 | " | —CH2—CF3 |
| 41 | " | —CH2—CH=CH2 |
| 42 | " | —CH2—C6H5 |
| 43 | " | —CH2—⟨C6H4⟩—CF3 |
| 44 | " | —(CH2)2—C6H5 |
| 45 | —N(piperazinyl)N—(CH2)2OH | —(CH2)2—C6H5 |
| 46 | —N(morpholinyl) | —(CH2)2—⟨C6H4⟩—F |
| 47 | —N(piperazinyl)N—(CH3) | —(CH2)2—⟨C6H4⟩—F |
| 48 | —N(thiomorpholinyl) | —(CH2)2—⟨C6H4⟩—F |

-continued

Pyrrolidone compounds of the formula:

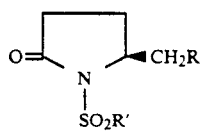

| EXAMPLE | R | R' |
|---|---|---|
| 49 | 5-chloropyrazin-2-yl (via CH linkage, N-attached pyrazine with Cl) | $-(CH_2)_2-C_6H_4-F$ (para) |
| 50 | morpholino (-N(CH$_2$CH$_2$)$_2$O) | $-(CH_2)_2-C_6H_4-CF_3$ (para) |
| 51 | morpholino | $-(CH_2)_3-C_6H_5$ |
| 52 | morpholino | $-CH=CH-C_6H_5$ |
| 53 | 4-methylpiperazin-1-yl | $-CH=CH-C_6H_5$ |
| 54 | 4-(2-hydroxyethyl)piperazin-1-yl | $-CH=CH-C_6H_5$ |
| 55 | 4-(3-chloropyrazin-2-yl)piperazin-1-yl | $-CH=CH-C_6H_5$ |
| 56 | isothiazolidin-2-yl 1,1-dioxide | $-CH=CH-C_6H_5$ |
| 57 | thiomorpholino | $-CH=CH-C_6H_5$ |
| 58 | $-N(CH_3)_2$ | $-CH=CH-C_6H_5$ |
| 59 | $-O-CO-N(C_2H_5)_2$ | $-CH=CH-C_6H_5$ |

-continued

Pyrrolidone compounds of the formula:

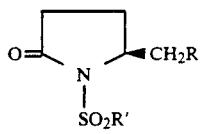

| EXAMPLE | R | R' |
|---|---|---|
| 60 | —N⟨O⟩ | —CH=CH—⟨C₆H₄⟩—Cl |
| 61 | —N⟨O⟩ | —CH₂—CH₂—NH₂ |
| 62 | —N⟨O⟩ | —CH₂—CH₂—N⟨O⟩ |

Following the procedure described in Example 1, first method, and using a starting material in the R form, all the compounds mentioned in Examples 1 to 62 are obtained in the R form, which compounds differ from the corresponding S compounds as regards their physical properties, only in their rotatory power.

EXAMPLE 63

Pharmacological Study a) Principle

On ageing, reduction in intrinsic cerebral reserves leads to an inability to respond to any new metabolic demand. In the case of a cerebral vascular accident, selective neuronal vulnerability appears in the cells that have the greatest metabolic demand. The common factor between these pathologies is the deficit of oxygen utilisation which most frequently leads to a deviation in the metabolism towards anaerobia.

In the search for new cerebroprotective compounds such conditions can be reproduced experimentally, and in acute manner, by hypoxia.

The analogy between hypoxia and cerebral disorders associated with ageing or with circulatory insufficiency is expressed especially by the following:
  reduction in energy reserves,
  lower resistance to stress,
  reduction in the oxygen-dependent synthesis of neurotransmitters,
  fall in memory capacity.

The compounds of the present invention were therefore tested for their ability to prolong the survival of cerebral tissue during acute hypoxia in mice.

Their effectiveness was compared with that of reference substances recognised as anti-hypoxic agents or as nootropic agents.

Moreover, their cerebroprotective anti-hypoxic effects were compared with possible cerebrovascular effects by the use of two complementary tests: acute cardiac arrest and acute anoxia under nitrogen in mice.

This comparison makes it possible to distinguish between the "pure" anti-hypoxic compounds, neuronal protectors, which have a cerebral tropism mainly during hypoxia, and the non-specific compounds which also manifest their protective effects in the case of cardiac ischaemia and/or in general anoxia. In the latter case, the systemic effect of a compound is most frequently due to vasodilatory and/or sedative effects.

b) Method

α) Acute Hypobaric Hypoxia

Male CD1 mice (Charles River), which have received the test compound 30 minutes beforehand by the i.p. route, are subjected to acute hypoxia of the hypobaric type. For that purpose, they are placed in a vessel in which the barometric pressure can be reduced rapidly (over 30 seconds) to 160 mbar. Air is renewed during the test in order to enable hypoxia to be provoked, and not asphyxia or anoxia, which could call for protection of a vascular origin. Under these conditions, brain death of the animals is obtained in approximately 15 seconds after hypoxic pressure has been reached.

The average survival time of a treated batch is compared with that of a control batch receiving only the solvent.

β) Acute Cardiac Ischaemia

Male CD1 mice (Charles River), which have received the test compound 30 minutes beforehand by the i.p. route, are subjected to a sudden cardiac arrest by the intravenous injection of a massive dose of $MgCl_2$ (0.1 ml of a solution of physiological serum saturated with $MgCl_2$). Under these conditions, brain death of the animals is obtained in approximately 20 seconds after the i.v. injection.

The average survival time of a treated batch is compared with that of a control batch receiving only the solvent.

γ) Acute General Anoxia under Pure Nitrogen

Male CD1 mice (Charles River), which have received the test compound 30 minutes beforehand by the i.p. route, are subjected to acute anoxia by inhalation of pure nitrogen. For that purpose, they are placed in a vessel of restricted volume (250 ml) in which pure nitrogen circulates at a high flow rate (2 l/minute), without overpressure. Under these conditions, brain death of the animals is obtained in approximately 24 seconds after the start of the anoxic flow.

The average survival time of a treated batch is compared with that of a control batch receiving only the solvent.

c) Results

Under these drastic experimental conditions, the reference compounds exert only a moderate anti-hypoxic effect or are accompanied by effects of equivalent intensity in one or in both of the complementary tests. In the latter case, apparent vasodilation and/or sedation accompany these non-specific effects.

The nootropic reference compounds, piracetam and its analogues, provide only slight protection against hypoxia for the brain. High doses are sometimes necessary to observe a significant increase in brain survival time.

| | | |
|---|---|---|
| Piracetam | 300 mg/kg | +5.3 sec. (+34%) |
| | 1000 mg/kg | +6.3 sec. (+40%) |
| Pramiracetam | 100 mg/kg | +3.3 sec. (+21%) |
| | 300 mg/kg | +5.6 sec. (+36%) |
| Oxiracetam | 100 mg/kg | +1.1 sec. (+6%) |
| Doliracetam | 30 mg/kg | +0.1 sec. (+1%) |
| | 100 mg/kg | +15.3 sec. (+107%) |

In the case of doliracetam, this protective effect at a dose of 100 mg/kg is accompanied by undesirable sedation, which distinguishes it from the other nootropic compounds. Moreover, the sedation is responsible for the anti-hypoxic effect.

Other reference compounds were studied. They were selected for their therapeutic indications of the cerebroprotective type. The following results were obtained:

| | | |
|---|---|---|
| Nizophenone | 3 mg/kg | +12.1 sec. (+86%) |
| Pyritinol | 100 mg/kg | +3.9 sec. (+27%) |
| Dihydroergotoxine | 10 mg/kg | +9.6 sec. (+68%) |
| Meclofenoxate | 100 mg/kg | +3.1 sec. (+22%) |

At the doses studied to obtain a marked anti-hypoxic effect, nizophenone and dihydroergotoxine have secondary effects, namely sedation and peripheral vasodilation, respectively.

The compounds of the invention, which do not have undesirable neuro-behavioural effects, are significantly effective against cerebral hypoxia, as the following examples show:

| | | |
|---|---|---|
| Example 17 | 100 mg/kg | +25.9 sec. (+159%) |
| Example 42 | 100 mg/kg | +14.5 sec. (+88%) |
| Example 53 | 100 mg/kg | +18.8 sec. (+156%) |
| Example 56 | 100 mg/kg | +10.5 sec. (+74%) |
| Example 57 | 100 mg/kg | +48.9 sec. (+345%) |

These neuroprotective, cerebral anti-hypoxic effects are exerted with a high degree of specificity, as is shown by a comparison of the results of the three tests described above, which results are listed in the table below. The results are expressed as absolute values of the increase in survival time (seconds).

| Compound | Dose (mg/kg) | Cerebral hypoxia | Cardiac arrest | General anoxia |
|---|---|---|---|---|
| Piracetam | 1000 | +6.3 | 0 | +1.6 |
| Pramiracetam | 100 | +3.3 | +0.4 | 0 |
| Doliracetam | 100 | +15.3 | +6.4 | +14.6 |
| Nizophenone | 3 | +12.1 | +10.5 | +10.7 |
| Pyritinol | 100 | +3.9 | +1.9 | +5.0 |
| Dihydroergotoxine | 10 | +9.6 | +5.3 | +10.1 |
| Prazosine | 3 | +3.9 | +4.4 | +6.9 |
| Example 17 | 100 | +25.9 | +4.3 | +10.6 |
| Example 42 | 100 | +14.5 | +4.3 | +7.0 |
| Example 53 | 100 | +18.8 | +3.4 | +9.1 |
| Example 56 | 100 | +10.5 | 0 | +2.8 |
| Example 57 | 100 | +48.9 | +15.5 | +13.8 |

Therefore, the compounds of the present invention have a powerful and selective anti-hypoxic effect. They differ, therefore, from the compounds used as reference, either in the intensity of their effects (as compared with piracetam, pramiracetam, pyritinol) or in their specificity owing to the absence of a sedative effect (as compared with doliracetam, nizophenone) or a vascular effect (as compared with dihydroergotoxine, prazosine). In the latter cases, the reference compounds have identical, if not superior, effects as regards cardiac arrest or general anoxia, which indicates an absence of major tropism for the brain or an indirect effect.

The compounds of the invention can therefore be effective against cerebral disorders associated with a lack of energy caused especially by insufficient oxygen intake, and associated with any metabolic neuronal deficiency.

We claim:

1. A compound selected from the group consisting of: Pyrrolidone compounds of the formula I:

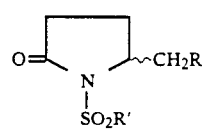

in which:

R is selected from the group consisting of:
  a) OR" and SR" groups in which R" is selected from the group consisting of:
    a hydrogen atom,
    a COR''' radical in which R''' is selected from the group consisting of:
      straight-chain and branched alkyl radicals having 1 to 4 carbon atoms, inclusive,
      an N ($R_1R_2$) radical in which $R_1$ and $R_2$, which are the same or different, are each selected from the group consisting of straight-chain and branched alkyl radicals having 1 to 5 carbon atoms, inclusive, or $R_1$ and $R_2$ together represent a polymethylene chain having 4 to 6 carbon atoms, inclusive, and such a chain containing an oxygen atom, so as to form together with the nitrogen atom to which they are bonded a heterocyclic radical selected from pyrrolidinyl, piperidino, and morpholino radicals;
    straight-chain and branched alkyl groups having 1 to 6 carbon atoms, inclusive and these groups containing one and more oxygen atoms, a hydroxy radical, or an —N (R₁R₂) radical in which R₁ and R₂ have the meanings defined above;

b) an —N (R₃R₄) radical in which:

R₃ and R₄, which are the same or different, are each selected from the group consisting of:
a hydrogen atom,
straight-chain and branched alkyl radicals having up to 6 carbon atoms and these radicals containing one or more oxygen atoms, a hydroxy radical, 0 COR′′′, or N (R₁R₂) radicals in which R′′′, R₁ and R₂ have the meanings defined above, or R₃ and R₄, together with the nitrogen atom to which they are bonded, form a heterocyclic radical of the formula:

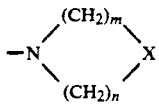

in which:
m is selected from zero, one and two;
n is an integer of from 1 to 3, inclusive, and
x is selected from the group consisting of:
a methylene radical (—CH₂—);
an oxygen or sulfur atom, or the radical SO₂;
an >N—R₅ radical in which R₅ is selected from the group consisting of:
alkyl radicals having 1 to 4 carbon atoms, inclusive,
a hydroxy alkyl radical having 1 to 4 carbon atoms, inclusive,
an (unsubstituted aryl) alkyl radical in which the alkyl moiety has 1 to 4 carbon atoms, inclusive, and such aralkyl radicals in which the aryl moiety is mono or polysubstituted by (C₁-C₄) alkoxy or a methylenedioxy radical,
unsubstituted aryl radicals and such aryl radicals mono or polysubstituted by halogen or (C₁-C₄) alkoxy radicals, and
heterocyclic radicals, having one or two heteroatoms, selected from thiazolyl, pyrimidinyl, pyrazinyl, pyridyl and quinolyl radicals, and such radicals mono or poly-substituted by halogen, trifluoromethyl, or (C₁-C₄) alkoxy radicals; and
a >CH—YZ radical in which:
Y is selected from oxygen and sulfur atoms, and
Z is selected from heterocyclic radicals having one or two heteroatoms as defined above;

R′ is selected from the group consisting of:
a) straight-chain and branched alkyl radicals having 1 to 4 carbon atoms, inclusive, such radicals containing a double bond, and such radicals mono or polysubstituted by hydroxy, trifluoromethyl, amino, —N (R₁R₂) as defined above, phenyl, halophenyl, (C₁-C₅-alkyl) phenyl, (C₁-C₅ alkoxy) phenyl, nitrophenyl, or aminophenyl radicals; and
b) aryl, halo-aryl, (C₁-C₅-alkyl)-aryl, (C₁-C₅-alkoxy)-aryl, nitroaryl, and amino-aryl radicals; and
the carbon located in the 5-position of the pyrrolidine ring, which is substituted by CH₂R, has the R or S configuration,
and physiologically-tolerable acid addition salts thereof.

2. A compound of claim 1 which is:
S-1-benzenesulphonyl-2-oxo-5-morpholinomethyl-pyrrolidine.

3. A compound of claim 1 which is:
S-1-benzenesulphonyl-2-oxo-5-[(4-methyl-1-piperazinyl)methyl]-pyrrolidine.

4. A compound of claim 1 which is:
S-1-benzenesulphonyl-2-oxo-5-[(4-metatrifluoromethyl-phenyl-1-piperazinyl)methyl]-pyrrolidine.

5. A compound of claim 1 which is:
S-1-methanesulphonyl-2-oxo-5-morpholinomethyl-pyrrolidine.

6. A compound of claim 1 which is:
S-1-benzenesulphonyl-2-oxo-5-{[4-(6-chloro-2-pyrazinyl)-1-piperazinyl]methyl}-pyrrolidine or its hydrochloride.

7. A compound of claim 1 which is:
S-1-benzylsuphonyl-2-oxo-5-morpholinomethyl-pyrrolidine or its hydrochloride.

8. A compound of claim 1 which is:
S-1-styrylsulphonyl-2-oxo-5-[(4-methyl-1-piperazinyl)-methyl]pyrrolidine.

9. A compound of claim 1 which is:
S-1-styrylsulphonyl-2-oxo-5-(2-sultamyl-methyl)-pyrrolidine.

10. A compound of claim 1 which is:
S-1-styrylsulphonyl-2-oxo-5-thiomorpholinomethyl-pyrrolidine.

11. A pharmaceutical composition useful in the alleviation of cerebral disorders associated with lack of energy due to insufficient oxygen intake or with a metabolic neuronal deficiency, containing as active ingredient an effective amount of a compound according to any of claims 1 through 10 together with a pharmaceutically-acceptable carrier or diluent.

12. A method for treating a living animal afflicted with a cerebral disorder associated with lack of oxygen due to insufficient oxygen intake or metabolic neuronal deficiency, comprising the step of administering to the said living animal an amount of a compound of any of claims 1 through 10 which is effective for alleviation of the said condition.

* * * * *

UNITED STATES PATENT AND TRADEMARK OFFICE
CERTIFICATE OF CORRECTION

PATENT NO. : 5,066,651
DATED : Nov. 19, 1991
INVENTOR(S) : Gilbert Regnier, Alain Dhainaut, Jean Lepagnol It is certified that error appears in the above-identified patent and that said Letters Patent is hereby corrected as shown below:

On the title page, Item [19]: "Regnir" should read --Regnier--.
Title Page, [75] Inventors:, line 1; "Regnir" should read --Regnier--.
Title Page [75] Inventors", line 3, 4; after "France", first occurrence, delete --Jean Lepagnol, both of Chatou, France--.

Column 7, line 25; " D :" should read -- $\frac{21}{D}$ : --.

Column 8, approximately line 37: "5[(4-" should read --5[(4- --.

This certificate supersedes the Certificate of Correction issued April 6, 1993.

Signed and Sealed this

Twenty-third Day of November, 1993

*Attest:*

BRUCE LEHMAN

*Attesting Officer*     *Commissioner of Patents and Trademarks*